(12) United States Patent
Kjell

(10) Patent No.: US 9,956,129 B2
(45) Date of Patent: May 1, 2018

(54) WEIGHT COVER

(71) Applicant: Novista Care of Sweden AB, Båstad (SE)

(72) Inventor: Sven-Inge Kjell, Båstad (SE)

(73) Assignee: Novista of Sweden AB, Båstad (SE)

( * ) Notice: Subject to any disclaimer, the term of this patent is extended or adjusted under 35 U.S.C. 154(b) by 350 days.

(21) Appl. No.: 14/763,034

(22) PCT Filed: Jan. 23, 2014

(86) PCT No.: PCT/SE2014/000009
§ 371 (c)(1),
(2) Date: Jul. 23, 2015

(87) PCT Pub. No.: WO2014/116163
PCT Pub. Date: Jul. 31, 2014

(65) Prior Publication Data
US 2015/0366734 A1    Dec. 24, 2015

(30) Foreign Application Priority Data
Jan. 25, 2013   (SE) ...................................... 1300066

(51) Int. Cl.
*A61H 1/00*   (2006.01)
*A61H 99/00*   (2006.01)
(Continued)

(52) U.S. Cl.
CPC ........... *A61H 1/008* (2013.01); *A47G 9/0207* (2013.01); *A47G 9/0223* (2013.01); *A61H 99/00* (2013.01);
(Continued)

(58) Field of Classification Search
CPC ........ A61H 1/008; A61H 15/00; A61H 99/00; A61H 2201/0134; A61H 2201/0157;
(Continued)

(56) References Cited

U.S. PATENT DOCUMENTS 4,839,934 A    6/1989   Rojas
6,199,232 B1 *  3/2001   Kocivar ............... A47G 9/0207
                                                      2/69.5

(Continued)

FOREIGN PATENT DOCUMENTS

| SE | 1300066-6 | 1/2013 |
|----|-----------|--------|
| WO | 2009123557 | 10/2009 |
| WO | 2012009739 | 1/2012 |

*Primary Examiner* — Glenn Richman
(74) *Attorney, Agent, or Firm* — Larson & Larson, P.A.; Justin P. Miller; Patrick A. Reid

(57) ABSTRACT

A weight cover (10) for therapeutic treatment has a plurality of elements (20) placed in a plurality of channels (12) between fabric layers of the weight cover to increase its weight. The channels are arranged in parallel along the length of the cover. The elements (20) are each configured as a closed case containing oblong fibers, which form weighted bands (20), and which follow the shape of the body of a user. The weighted bands contain a constant number of fibers per length unit. The weight cover has an insulating textile layer (42). The weighted bands (20) has a first fastening mean (22) that is in engagement with a second fastening mean (44) of the weight cover (10).

14 Claims, 3 Drawing Sheets

(51) Int. Cl.
*A61M 21/02* (2006.01)
*A47G 9/02* (2006.01)
*A61H 15/00* (2006.01)
*A61M 21/00* (2006.01)

(52) U.S. Cl.
CPC ............. *A61M 21/02* (2013.01); *A61H 15/00* (2013.01); *A61H 2201/0134* (2013.01); *A61H 2201/0157* (2013.01); *A61H 2201/168* (2013.01); *A61M 2021/0022* (2013.01)

(58) Field of Classification Search
CPC ............ A61H 2201/168; A61M 21/02; A61M 2021/0022; A47G 9/0223; A47G 9/0207
See application file for complete search history.

(56) References Cited

U.S. PATENT DOCUMENTS

| | | | | |
|---|---|---|---|---|
| 6,243,896 B1* | 6/2001 | Osuna | .................. | A47G 9/0207 |
| | | | | 5/482 |
| 2006/0174410 A1* | 8/2006 | Mastandrea, Jr. | ... | A01K 1/0353 |
| | | | | 5/482 |
| 2011/0047698 A1 | 3/2011 | Parker | | |
| 2016/0037944 A1* | 2/2016 | Savignano | ............. | A47G 9/062 |
| | | | | 5/644 |

\* cited by examiner

WEIGHT COVER

CROSS-REFERENCE TO RELATED APPLICATION

This application claims priority to PCT Application Number PCT/SE2014/000009, filed Jan. 23, 2014, published as WO 2014/116163, which in turn claims priority to Swedish Patent Application Number SW1300066-6 filed Jan. 25, 2013.

TECHNICAL FIELD

The present invention relates to a weighted cover adapted for therapeutic treatment, where the weighted cover comprises a plurality of elements that are arranged within channels of said cover for increasing the weight thereof.

BACKGROUND OF THE INVENTION

Persons suffering from anxiety, restlessness or sensorimotor disorders have difficulties to relax, finding calmness and to sleep. For example, people with cognitive functional disorders have problems with time perception, to remember and to plan their activities. Especially, children having ADHD- or Asperger syndrome have difficulties in learning, with comprehension and to solve problems.

It is known that a weight cover may give alleviation or relief of the above mentioned discomforts when used as a sleeping cover during the night, or when wrapped around the body for relaxation during the day. The weight cover offers a tactile stimulation by its heaviness that has a positive effect on both the surface and profound tactility of the body, which will affect the central nervous system. The tactile experience enhances the body image, since it assists in marking the boundary of the body, which will provide the user with a feeling of security and an experience of restfulness.

Investigations have shown that a pressure against the body stimulates the release of bodily-specific substances, such as oxytocin, which leads to a calming influence on the person. If the pressure is adapted to follow the shape of the body, the tactile stimulation increases and enhances the benefic result for the user. Especially for persons suffering from autism, dementia, hyperactivity or having problems regarding sensory impressions, the beneficial effects related to the use of a weight cover have been confirmed by users, relatives and health care providers.

Currently known weight covers have various types of fillings in pockets of said covers, for example plastic balls, sand, grits, popcorns, metallic balls, etc. The problem with such types of fillings is that it is difficult to keep a controlled steady pressure, which follows the shape of the body of a person, since the filling falls down toward a lowest part of the pockets. Other drawbacks of the known weight covers are the ungainliness when handling them, such as at folding and storing, or the difficulty to control the ability to keep their temperature. Another disadvantage is to maintain sanitary requirements, since the fillings do not allow ordinary washing in a washing machine.

The patent document SE 532 402 describes a weighted cover for therapeutic treatment comprising linked elements having a form like a chain, which are placed in longitudinal or transversal channels of the cover for increasing the weight thereof. The chains are fastened at the end of the cover by clenching means, or by means comprising a loop and a ribbon. Due to the mounting of the chains by loops, the pressure of the cover will not be uniformly distributed along the length thereof. A serious drawback of a weight cover comprising chains, is the risk of that the person using the cover can hurt himself or other persons. Easily accessible objects of metallic should be avoided in environments for treatment of persons suffering from any type of behavior disorders or dysfunctions.

There is a need of a weight cover that is secure and provides a desired pressure increasing effect for the user, and which is comfortable for the user regarding both body adaption and temperature. Further, there is a need of a weight cover that can fulfill sanitary requirements, and which is easy to wash and handle, and to store when not in use.

SUMMARY OF THE INVENTION

In the description of the invention below, a cover is defined as a type of a blanket for therapeutic treatment, which for example is used at sleep or at rest.

An object of the present invention is to eliminate the above mentioned drawbacks and to provide a weight cover having the features according to claim 1.

A more specific object of the present invention is to provide a weight cover for therapeutic treatment comprising a plurality of elements for increasing the weight of the cover, wherein said elements are arranged in a plurality of corresponding channels between a first and a second fabric layer of the weight cover.

The channels are arranged essentially in parallel along the length and/or the width of said cover. Each of the elements is configured as a closed case comprising fibers along the length thereof, which forms a weighted band that follows the body of a user of the cover. Said case is perpendicularly sewn across its length, in such way that said weighted band contains a constant number of fibers per length unit. The fibers are oblong and are arranged lengthways within the case. They are made of polyester or of a similar type of polymeric material. The amount of fibers can be adapted to the need of a user, for example, the cover can be made heavier for a grown up than for a child. Each of the weighted bands has a weight of about 500-1000 gram.

The weighted bands have at least a first fastening mean arranged at each of their short sides, respectively, which is in engagement with at least a second fastening mean. Said at least second fastening mean is arranged in transversal bands, which are sewn to each of the short sides of the first fabric layer of the weighted cover. The fastening means are facing the second fabric layer of the weighted cover, which gives an increased comfort to a user of the cover, since the fastening means are not in touch with her or him. For example, the first fastening mean can be a female part of a push-button and the second fastening mean is then a male part of said push-button. Alternatively, the first fastening mean can be a button or a ribbon, and the second fastening mean is then a hole for a button or a loop, respectively.

The weight cover has a third fabric layer and an insulating textile layer arranged between the second fabric layer and said third fabric layer, which three layers are stitched together along their short sides, respectively, forming a unit. This unit is fastened along its long sides to the first fabric layer by an enfolding side band in such way that the channels of the weight cover are left opened.

According to an alternate embodiment, the weighted bands are attached to the short sides of the first fabric layer by seams. In this case, the fastening means are eliminated.

Further objects, features and advantages of the present invention will appear from the following detailed description, from the attached drawings and from the dependent claims.

BRIEF DESCRIPTION OF THE DRAWINGS

In order to explain the invention, embodiments of the invention will be described below with reference to the drawings, in which.

Same reference numerals have been used to indicate the same parts in the figures to increase the readability of the description and for the sake of clarity.

DESCRIPTION OF EMBODIMENTS OF THE INVENTION

A weight cover 10 according to the invention will be described below with reference to the drawings. The weight cover 10 is intended for use in therapeutic treatment of persons who for example are suffering from sensorimotor disorders, cognitive functional disorders, restlessness or anxiety. Persons having different types of dysfunctionality, such as ADHD- or Asperger syndrome, will faster and easier reach relaxation at sleep or rest when using the weight cover, which has been shown by investigations.

The purpose of the weight cover according to the invention is to increase the pressure against the body to provide a human being a better idea of, and feeling for, the boundaries of its own body. The heaviness of the inventive weight cover follows the contour of the body due to the construction of the cover, which increases the tactile stimuli, and consequently the positive effect of relaxation is increased for the user.

Figure 1:
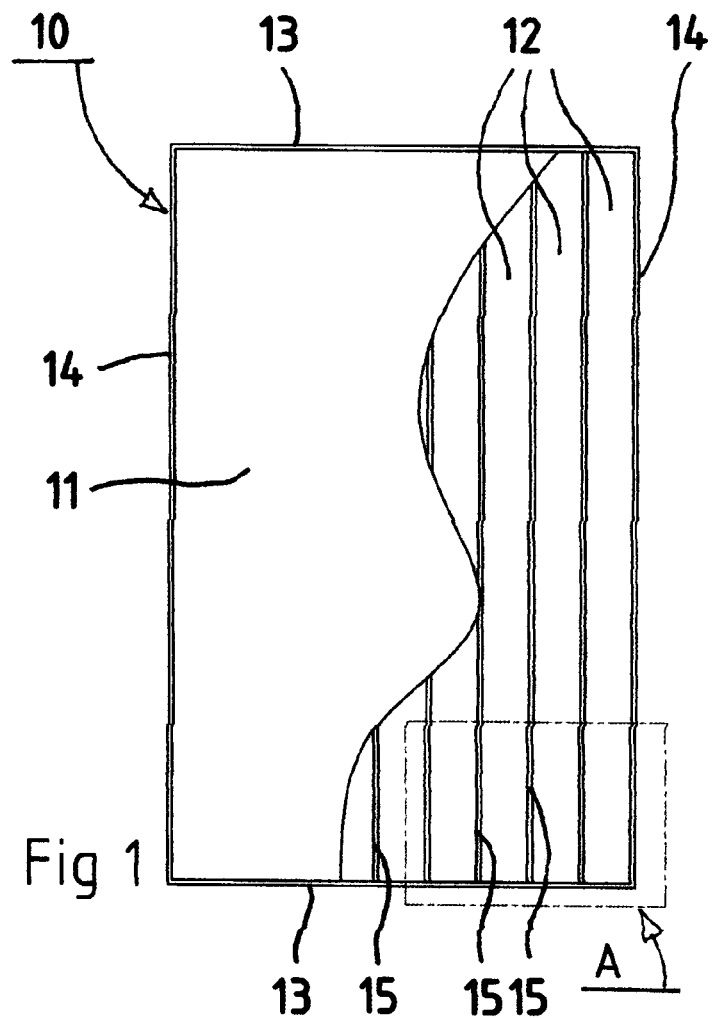
FIG. 1 is a schematic horizontal view of a weight cover according to the invention having a first fabric layer partly broken away.

FIG. 1 illustrates schematically a weight cover 10 according to a first embodiment of the invention having a first fabric layer 11 partly broken away. The weight cover 10 has a first fabric layer 11 and a second fabric layer 40 (see FIG. 4). The cover 10 has a third fabric layer 41 (see FIG. 4), which is arranged facing the second fabric layer 40. An insulating textile layer 42 (see FIG. 4) is arranged between the fabric layers 40 and 41, respectively.

A plurality of channels 12 are arranged lengthways, between the first fabric layer 11 and the second fabric layer 40. The channels 12 are opening at each of the short sides of the cover 10. Each of the long sides of the cover 10 is closed. The channels 12 are formed by seams 15, which are sewn through the three layers of fabrics 11, 40, 41 and the insulating textile layer 42 and in parallel with the long sides 14 of the cover 10, which will be explained in detail below.

Figure 2:
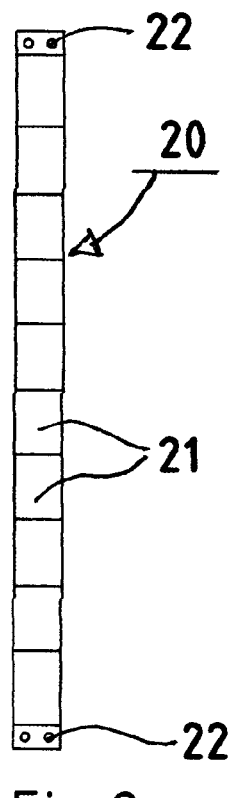
FIG. 2 is a schematic horizontal view of a weighted band that will be positioned in a channel of the weight cover according to FIG. 1.

FIG. 2 shows one of several elements 20, denoted a weighted band below, which will be placed into the channels 12 of the weight cover 10 to increase the weight thereof. The weighted band is configured or formed as a closed case containing fibers along its length. The cases are made of a dense web or tissue of cotton, of synthetic material or of a mixture thereof, and are flame-proof. The fibers are made of polyester or of a similar polymeric material. According to a first embodiment, the fibers have an oblong shape and are arranged lengthwise within the case. According to an alternative embodiment the fibers may have another shape.

Each case is sewn perpendicular across its length, forming a plurality of closed compartments or pockets 21, which results in that each case contains a constant number of fibers per length unit. Each weighted band has a weight of 500-1000 gram. Each of the weighted bands 20 has at least one fastening means 22 to be arranged to the weight cover 10, which will be explained below.

Figure 3:
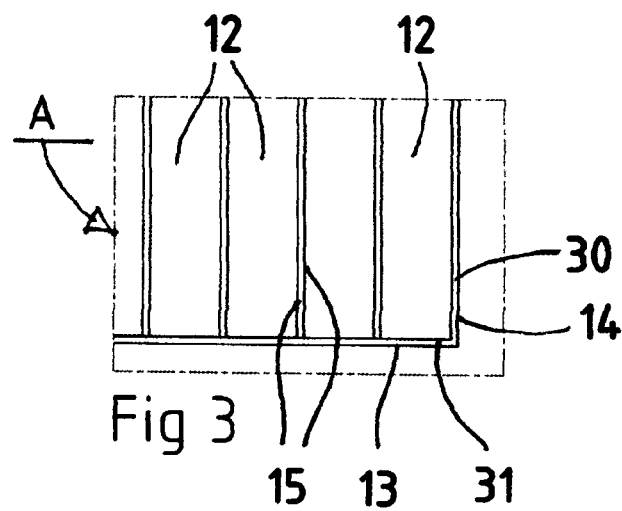
FIG. 3 is a schematic view of an enlarged section A of the weight cover according to FIG. 1 having the first fabric layer removed.

FIG. 3 shows an enlargement of a section A of the weight cover 10. The channels 12 are uniformly arranged across the width of said cover 10. There could be interspaces between said channels, which are formed by stitching the seams 15 dually at a distance from each other, e.g. 5-50 mm, or more preferably 10-30 mm. The width of the channels 12 can be arbitrary, e.g. 30-100 mm. The cover 10 has side bands 30 sewn along each of the long sides 14 of the cover 10 enfolding these, which are keeping together the three fabric layers 11, 40, and 41, and the insulating textile layer 42. Similar side bands 31 are enclosing the short sides of the second fabric layer 40 and the third fabric layer 41 having the insulating textile layer 42 in between each other for keeping these three layers together at the short sides 13 of the weight cover 10.

Figure 4:
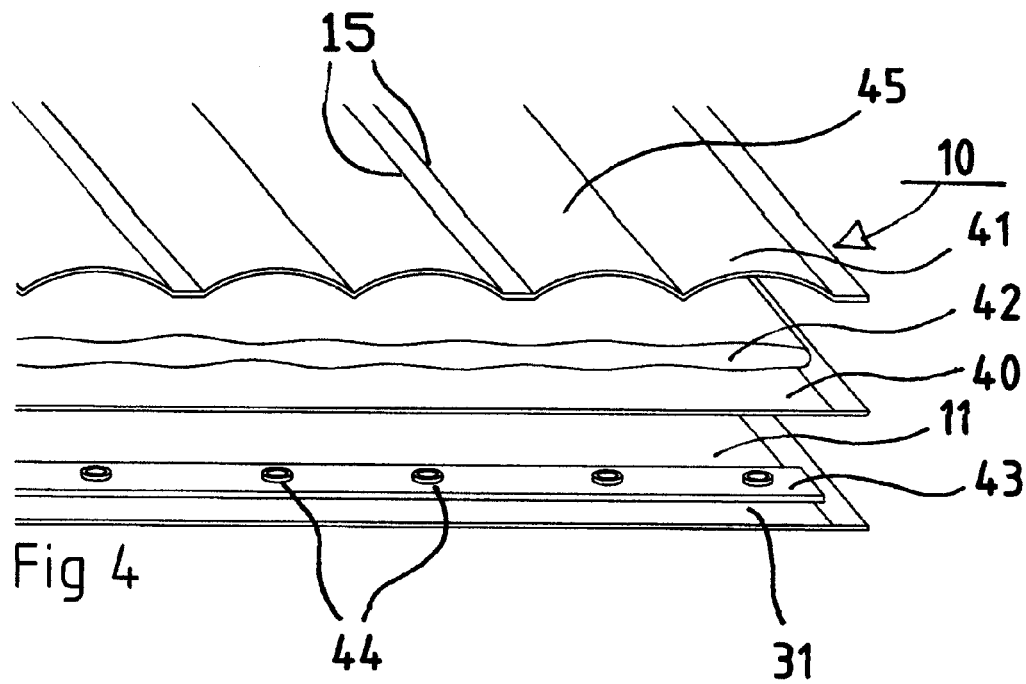
FIG. 4 is a schematic exploded view showing a part of the weight cover according to FIG. 1 from a short side thereof.

FIG. 4 shows an exploded view of a part of the weight cover 10, according to FIG. 1, from a short side thereof. The first fabric layer 11 forms a first outer surface of the weight cover 10. Transversal bands 43 are arranged to the first fabric layer, along one of their long sides, respectively, e.g. by seams or glue, below the side bands 31 that are enfolding the short sides of the first fabric layer 11. First fastening means 44 for fastening the weighted bands 20 are arranged at the transversal bands 43. The transversal bands 43 are made of polyamide, such as nylon or of a similar material. Further, FIG. 4 shows the second fabric layer 40, the insulating textile material 42, and the third fabric layer 41, which forms a second outer surface of the weight cover 10. Optionally, a seem 45 can be applied to the fabric layer 41 and to the insulating textile layer 42 to keep the last one in position before further manufacture of the cover.

At manufacture of the weight cover 10, firstly the transversal bands 43 are arranged with one of their long sides below the side bands 31, which will enfold the short sides of the fabric layer 11. Each of the transversal bands 43 and side bands 31, respectively, are sewn together with the fabric layer 11. The third fabric layer 41 is arranged towards the second fabric layer 40 having the insulating textile layer 42 arranged between the fabric layers 40, 41, forming a unit. Side bands 31 are arranged along the short sides of said unit and are fixed by sewing to enclose this one.

The second fabric layer 40 is placed toward the first fabric layer 11 in such way that the transversal bands 43 are facing the fabric layer 40. The channels 12 are formed between the fabric layers 11 and 40 by seams 15, sewn through said unit and the fabric layer 11. The seams 15 are not sewn all the way until the short sides 13 of the weight cover 10; they are ending at the transversal bands 43. Finally, enfolding side bands 30 are arranged along each of the long sides 14 of the cover for keeping all layers together. The channels 12 are freely opened at both short sides 13 of the cover 10 to enable the arrangement of the weighted bands into the channels 12.

First fastening mean 22 are arranged at each end of the weighted bands. Second fastening mean 44, which will be brought in engagement with the first fastening mean 22, are arranged in the transversal bands 43. For example, the fastening means can be a female part and a male part, respectively, of a push-button, or a button and a hole or a slit, or a co-operating ribbon and a loop.

Figure 5:
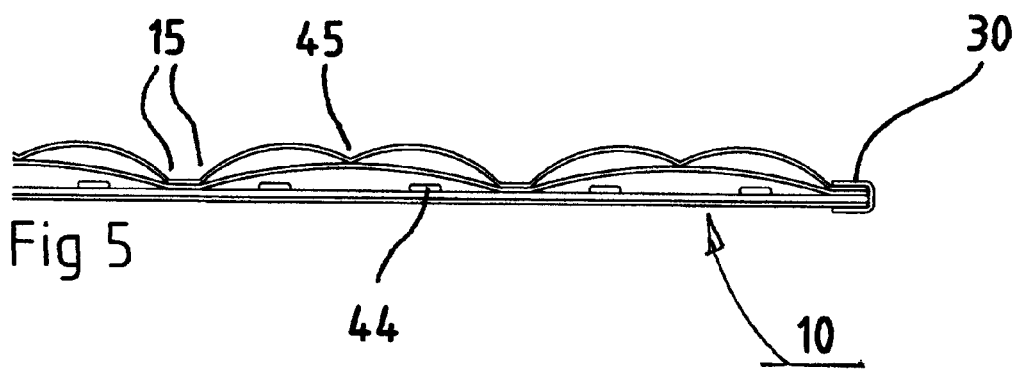
FIG. 5 is a schematic vertical view showing a part of the weight cover according to FIG. 1 from a short side thereof.

FIG. 5 shows schematically a vertical view of the weight cover 10 according to FIG. 1, from a short side thereof, where the cover has double seams 15 between the channels 12.

Figure 6:
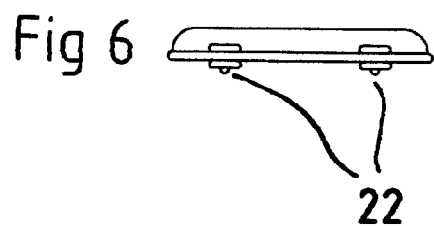
FIG. 6 is a schematic view of a weighted band, seen from a short side thereof, which will be placed in a channel of the weight cover according to FIG. 1.

FIG. 6 shows a weighted band 20, from a short side view thereof, having first fastening means 22, which will be placed into a channel 12 of the weight cover 10 according to FIG. 1.

Figure 7:
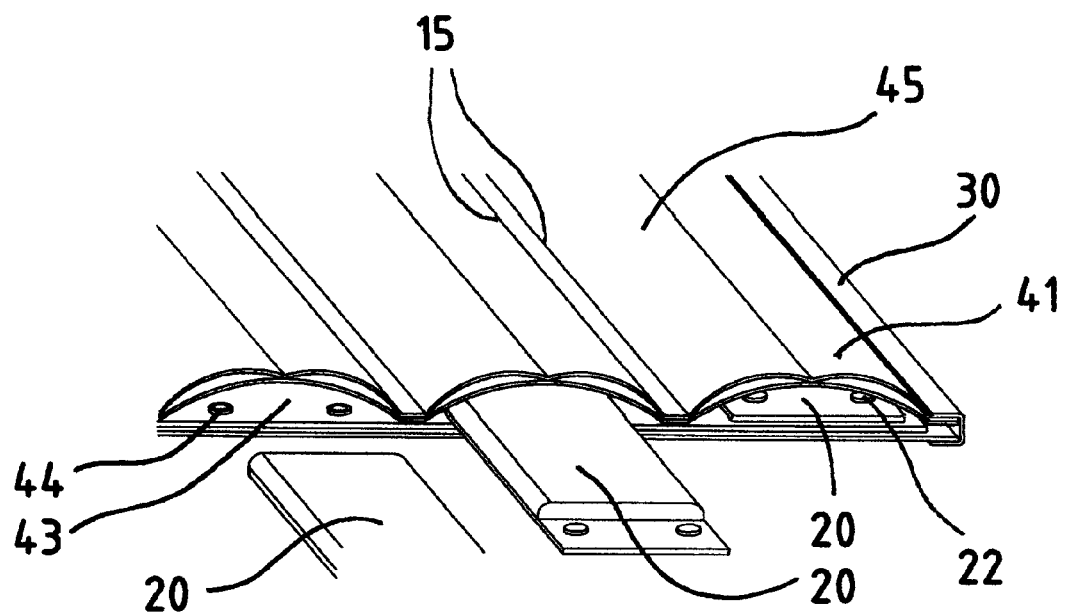
FIG. 7 is a schematic view of a part of the weight cover according to FIG. 1 showing an arrangement of weighted bands into the channels of the weight cover according to FIG. 1.

At arrangement of the weighted bands 20 into the channels 12, these are inserted into the channels 12 and are fastened at both of their ends by the first 22 and second 44 fastening means, as shown in FIG. 7. Each of the weighted bands 20 can have one or several first fastening means 22.

According to an alternate embodiment, the weighted bands are arranged to the first fabric layer by a seam at each of the short sides thereof. In this case, the transversal bands 43 can be omitted.

The fabric layers 11, 40, and 41, respectively, are made of a flame-proof textile material, preferably a cotton web or a polyester material. The insulating textile layer 42 can have various thicknesses depending on the time of the year, e.g. 10-15 mm. The weight cover as described can be manufactured in different sizes, depending on if the user is an adult or a child. For example, the cover can have a width of 1000-15000 mm and a length of 1500-2300 mm.

In an alternate embodiment, the weight cover can comprise two parts, where each of the parts has a width of 500-750 mm and a length of 1500-2300 mm. In this case, the two parts are connected by means of e.g. a zipper or another type of joining means. The main reason for having two parts is to bring down the size of the cover, which will facilitate the handling thereof, e.g. at washing.

The use of the weight cover can be adapted in weight and size to the specific needs of a person, e.g. as a sleeping cover for the night having a bed sheet around, or as wrapped around shoulders and back, when the person is sitting in a sofa or an armchair. Every channel does not have to contain a weighted band; some of the channels may be empty. Alternatively, the weighted bands of different channels can vary in heaviness for creating a various pressure across the cover. It is easy to adapt the total weight to the user for whom the cover is intended and customized for.

Due to the construction of the weight cover 10 having the elements of heaviness shaped as weighted bands, which are easily removable, the weight cover 10 is easy to store when not in use and simultaneously easy to bring or move. Also, the cover is easy to handle when washing, since the weighted bands can be removed from the channels, and then be washed and dried separately.

The total benefit gained from the weight cover as presented, can increase the possibility to effectively treat persons having severe dysfunctionality during rest and sleep. Simultaneously, requirements related to flexibility at weight adaption, hygiene aspects and ability to handle the cover are fulfilled.

The description as presented should be seen as an illustration of the principals of the invention and is not intended to limit the invention to the specific embodiment described.

As easily understood by the skilled man within the art, there can be alternate embodiments within the scope of protection of the invention. For example, an alternate embodiment of the weight cover can comprise the first and second fabric layer, but not the third one. Another embodiment can comprise channels arranged in parallel along the short sides of the cover, instead of along the long sides as described above.

In the claims, the term "comprise/comprising" does not exclude the presence of other elements or steps. Reference signs in the claims are provided as a clarifying example and shall not be construed as limiting the scope in any way.

The invention claimed is:

1. A weight cover for therapeutic treatment comprising:
   a. a plurality of elements to increase the weight of the cover,
   b. wherein said elements are positioned in a plurality of channels between a first and a second fabric layer of the weight cover where said channels are arranged essentially in parallel along the length of the cover and/or width of the cover,
   c. whereby bands of heaviness are provided across the cover, wherein each of said plurality of elements is configured as a closed case containing fibers along the length thereof forming a weighted band, which follows the shape of the body of a user of the weight cover;
   d. said case is sewn perpendicularly across the length thereof, and:
   e. further wherein the weighted band contains a constant number of fibers per length unit.

2. The weight cover of claim 1 wherein:
   said fibers are oblong and are arranged lengthwise within the case.

3. The weight cover of claim 1 wherein:
   said fibers are made of polyester or of a similar type of polymeric material.

4. The weight cover according to claim 1 wherein:
   said weighted band has a weight of 500-1000 gram.

5. The weight cover according to claim 1, wherein:
   said weighted band has at least a first fastening means arranged at each of the short sides thereof that will be in engagement with at least one second fastening means, which is arranged at transversal bands arranged at each short side of the first fabric layer of the weight cover facing the second fabric layer of the weight cover.

6. The weight cover of claim 1, wherein:
   a. said weight cover comprises a third fabric layer, which is arranged toward the second fabric layer, and an insulating textile layer that is arranged between the second fabric layer and said third layer,
   b. further wherein said third fabric layer, the insulating textile layer and the second fabric layer are sewn together along their short sides forming a unit, which unit is arranged with a side band along its long sides to the first fabric layer so that the channels of the weighted cover are freely opened.

7. The weight cover of claim 5, wherein:
   the first fastening means is a female part of a push-button and the second fastening mean is a male part of a push-button.

8. The weight cover of claim 5, wherein:
the first fastening means is a button and the second fastening means is a button hole or a slit.

9. The weight cover of claim 1, wherein:
the weighted bands are attached to the short sides of the first fabric layer by seams.

10. The weight cover of claim 2, wherein:
said fibers are made of polyester or of a similar type of polymeric material.

11. The weight cover of claim 2, wherein:
a. said weight cover comprises a third fabric layer, which is arranged toward the second fabric layer, and an insulating textile layer that is arranged between the second fabric layer and said third layer,
b. further wherein said third fabric layer, the insulating textile layer and the second fabric layer are sewn together along their short sides forming a unit, which unit is arranged with a side band along its long sides to the first fabric layer so that the channels of the weighted cover are freely opened.

12. The weight cover of claim 3, wherein:
a. said weight cover comprises a third fabric layer, which is arranged toward the second fabric layer, and an insulating textile layer that is arranged between the second fabric layer and said third layer,
b. further wherein said third fabric layer, the insulating textile layer and the second fabric layer are sewn together along their short sides forming a unit, which unit is arranged with a side band along its long sides to the first fabric layer so that the channels of the weighted cover are freely opened.

13. The weight cover of claim 4, wherein:
a. said weight cover comprises a third fabric layer, which is arranged toward the second fabric layer, and an insulating textile layer that is arranged between the second fabric layer and said third layer,
b. further wherein said third fabric layer, the insulating textile layer and the second fabric layer are sewn together along their short sides forming a unit, which unit is arranged with a side band along its long sides to the first fabric layer so that the channels of the weighted cover are freely opened.

14. The weight cover of claim 5, wherein:
a. said weight cover comprises a third fabric layer, which is arranged toward the second fabric layer, and an insulating textile layer that is arranged between the second fabric layer and said third layer,
b. further wherein said third fabric layer, the insulating textile layer and the second fabric layer are sewn together along their short sides forming a unit, which unit is arranged with a side band along its long sides to the first fabric layer so that the channels of the weighted cover are freely opened.

* * * * *